(12) United States Patent
Sarfaty et al.

(10) Patent No.: US 7,042,558 B1
(45) Date of Patent: May 9, 2006

(54) EDDY-OPTIC SENSOR FOR OBJECT INSPECTION

(75) Inventors: Moshe Sarfaty, Cupertino, CA (US); Ramaswamy Sreenivasan, San Jose, CA (US); Jaim Nulman, Palo Alto, CA (US)

(73) Assignee: Applied Materials, Santa Clara, CA (US)

( * ) Notice: Subject to any disclaimer, the term of this patent is extended or adjusted under 35 U.S.C. 154(b) by 105 days.

(21) Appl. No.: 10/619,171

(22) Filed: Jul. 10, 2003

Related U.S. Application Data

(62) Division of application No. 09/812,329, filed on Mar. 19, 2001, now Pat. No. 6,608,495.

(51) Int. Cl.
*G01N 21/00* (2006.01)
*G01R 19/00* (2006.01)

(52) U.S. Cl. .................. 356/72; 356/73; 324/244.1; 324/752; 324/765

(58) Field of Classification Search ............ 356/72–73; 324/230, 752, 765, 96; 451/6
See application file for complete search history.

(56) References Cited

U.S. PATENT DOCUMENTS

| | | |
|---|---|---|
| 4,005,359 A | 1/1977 | Smoot |
| 4,112,365 A | 9/1978 | Larson et al. |
| 4,303,885 A | 12/1981 | Davis et al. |
| 4,467,281 A | 8/1984 | Davis et al. |
| 4,556,845 A | 12/1985 | Strope et al. |
| 4,673,877 A | 6/1987 | Sakamoto et al. |
| 4,715,007 A | 12/1987 | Fujita et al. |
| 4,716,366 A | 12/1987 | Hosoe et al. |
| 4,849,694 A | 7/1989 | Coates |
| 4,963,500 A | 10/1990 | Cogan et al. |
| 4,977,853 A | 12/1990 | Falcoff et al. |
| 5,001,356 A * | 3/1991 | Ichikawa ................. 356/630 |
| 5,003,262 A | 3/1991 | Egner et al. |
| 5,081,796 A | 1/1992 | Schultz |
| 5,140,265 A * | 8/1992 | Sakiyama et al. ......... 324/220 |
| 5,213,655 A | 5/1993 | Leach et al. |
| 5,237,271 A | 8/1993 | Hedegren |
| 5,343,146 A | 8/1994 | Koch et al. |
| 5,355,083 A | 10/1994 | George et al. |
| 5,357,331 A | 10/1994 | Flockencier |
| 5,413,941 A | 5/1995 | Koos et al. |
| 5,427,878 A | 6/1995 | Corliss |
| 5,433,651 A | 7/1995 | Lustig |
| 5,451,863 A | 9/1995 | Freeman |
| 5,511,005 A | 4/1996 | Abbe et al. |
| 5,525,903 A | 6/1996 | Mandl et al. |

(Continued)

FOREIGN PATENT DOCUMENTS

EP 0 460 348 A 12/1991

(Continued)

*Primary Examiner*—Layla G. Lauchman
(74) *Attorney, Agent, or Firm*—Fish & Richardson

(57) ABSTRACT

A sensor enables simultaneous or sequential eddy current and optical reflectance measurements of conducting film by providing an eddy current inspection coil and a first and a second optical fiber extending axially through the coil. The eddy current inspection coil is excited by a radio frequency generator and induces eddy currents in the conducting film which are sensed using a detector. The conducting film is illuminated by a first optical fiber, and light which is reflected from the conducting film is transmitted by a second optical fiber to a detector. The combined use of electrical and optical reflectance signals provides a single probe unit that measures both dielectric and conducting transparent and semi-transparent films.

24 Claims, 5 Drawing Sheets

U.S. PATENT DOCUMENTS

| | | |
|---|---|---|
| 5,541,510 A | 7/1996 | Danielson |
| 5,559,428 A | 9/1996 | Li et al. |
| 5,605,760 A | 2/1997 | Roberts |
| 5,609,511 A | 3/1997 | Moriyama et al. |
| 5,640,242 A | 6/1997 | O'Boyle et al. |
| 5,644,221 A | 7/1997 | Li et al. |
| 5,658,183 A | 8/1997 | Sandhu et al. |
| 5,660,672 A | 8/1997 | Li et al. |
| 5,663,797 A | 9/1997 | Sandhu |
| 5,672,091 A | 9/1997 | Takahashi et al. |
| RE35,703 E | 12/1997 | Koch et al. |
| 5,708,506 A | 1/1998 | Birang |
| 5,719,495 A | 2/1998 | Moslehi |
| 5,730,642 A | 3/1998 | Sandhu et al. |
| 5,731,697 A | 3/1998 | Li et al. |
| 5,733,171 A | 3/1998 | Allen et al. |
| 5,762,537 A | 6/1998 | Sandhu et al. |
| 5,791,969 A | 8/1998 | Lund |
| 5,807,165 A | 9/1998 | Uzoh et al. |
| 5,838,447 A | 11/1998 | Hiyama et al. |
| 5,851,135 A | 12/1998 | Sandhu et al. |
| 5,865,666 A | 2/1999 | Nagahara |
| 5,872,633 A | 2/1999 | Holzapfel et al. |
| 5,889,401 A | 3/1999 | Jourdain et al. |
| 5,893,796 A | 4/1999 | Birang et al. |
| 5,899,792 A | 5/1999 | Yagi |
| 5,911,619 A | 6/1999 | Uzoh et al. |
| 5,913,713 A | 6/1999 | Cheek et al. |
| 5,929,994 A | 7/1999 | Lee et al. |
| 5,948,203 A | 9/1999 | Wang |
| 5,949,927 A | 9/1999 | Tang |
| 5,964,643 A | 10/1999 | Birang et al. |
| 6,004,187 A | 12/1999 | Nyui et al. |
| 6,034,781 A | 3/2000 | Sarfaty et al. |
| 6,068,539 A | 5/2000 | Bajaj et al. |
| 6,071,178 A | 6/2000 | Baker, III |
| 6,120,348 A | 9/2000 | Fujita et al. |
| 6,159,073 A | 12/2000 | Wiswesser et al. |
| 6,179,709 B1 | 1/2001 | Redeker et al. |
| 6,190,234 B1 | 2/2001 | Swedek et al. |
| 6,254,459 B1 | 7/2001 | Bajaj et al. |
| 6,280,289 B1 | 8/2001 | Wiswesser et al. |
| 6,296,548 B1 | 10/2001 | Wiswesser et al. |
| 6,309,276 B1 | 10/2001 | Tsai et al. |
| 6,407,546 B1 | 6/2002 | Le et al. |
| 6,431,949 B1 | 8/2002 | Ishikawa et al. |
| 6,433,541 B1 * | 8/2002 | Lehman et al. ............. 324/230 |
| 6,448,795 B1 * | 9/2002 | Ermakov et al. ........... 324/724 |
| 6,458,014 B1 | 10/2002 | Ishikawa et al. |
| 6,558,229 B1 | 5/2003 | Kimura et al. |
| 6,563,308 B1 | 5/2003 | Nagano et al. |
| 6,575,825 B1 | 6/2003 | Tolles et al. |
| 6,586,337 B1 | 7/2003 | Parikh |
| 6,621,264 B1 | 9/2003 | Lehman et al. |
| 6,663,469 B1 | 12/2003 | Kimura et al. |
| 6,707,540 B1 | 3/2004 | Lehman et al. |
| 6,878,038 B1 * | 4/2005 | Johansson et al. ............. 451/6 |
| 6,921,466 B1 * | 7/2005 | Hongo et al. ............... 204/198 |
| 2001/0008827 A1 | 7/2001 | Kimura et al. |
| 2002/0002029 A1 | 1/2002 | Kimura et al. |
| 2002/0013124 A1 | 1/2002 | Tsujimura et al. |
| 2002/0077031 A1 | 6/2002 | Johansson et al. |
| 2002/0098777 A1 | 7/2002 | Laursen et al. |
| 2002/0164925 A1 | 11/2002 | Swedek et al. |

FOREIGN PATENT DOCUMENTS

| | | | |
|---|---|---|---|
| EP | 0 663 265 A1 | | 7/1995 |
| EP | 0 640 438 A1 | | 9/1995 |
| EP | 0 738 561 A1 | | 10/1996 |
| EP | 0 881 040 A2 | | 12/1998 |
| EP | 0 881 484 A2 | | 12/1998 |
| EP | 0 402 527 A2 | | 12/2000 |
| EP | 1 116 552 A2 | | 7/2001 |
| JP | 1-136009 | * | 5/1989 |
| JP | 3-295409 | * | 12/1991 |
| JP | 7-091948 | * | 4/1995 |
| WO | 01/46684 | | 6/2001 |
| WO | 01/89765 | | 11/2001 |

* cited by examiner

EDDY-OPTIC SENSOR FOR OBJECT INSPECTION

This application is a division of U.S. patent application Ser. No. 09/812,329, filed Mar. 19, 2001 now U.S. Pat. No. 6,608,495, the entire disclosure of which is incorporated by reference.

BACKGROUND OF THE INVENTION

1. Field of the Invention

The present invention relates to a sensor for the efficient inspection and measurement of objects such as semiconductor wafers upon which dielectric and conducting films are deposited.

2. Description of the Related Art

In the process of manufacturing integrated circuits, films are deposited on semiconductor wafers, etched, and overlaid by additional films to create the integrated circuits. The films may be either conducting metal films or dielectric films. Quality and thickness of a particular film layer is critical to the manufacturing process, and it is of particular interest to measure the thickness of a film layer quickly and accurately. Two types of measurement techniques are commonly used to measure thickness. Dielectric films are transparent and thickness may be measured using optical reflectance. Conducting metal film thickness may be measured using eddy current sensing techniques. Further, if the conducting metal film is thin enough, it is transparent or semi-transparent which allows the thickness of the film also to be measured using optical reflectance. Both techniques are known and used in the industry.

Optical reflectance may be used to determine characteristics such as thickness, index of refraction and index of extinction of transparent and semi-transparent films. Metal films with a thickness greater than a few tens of nanometers tend to be optically opaque to light having wavelengths between 200 and 1100 nanometers. As a result, optical reflectance measurements are ineffective to determine thickness for such films. Eddy current sensing may be used to measure sheet resistance, which is correlative of such electrically conducting film thickness. Thus eddy current sensing generally may be used to measure thick conducting films and optical reflectance sensing generally may be used to measure thin conducting films that are transparent or semi-transparent.

Eddy current sensing techniques do not work for measuring thickness of films which do not conduct electricity sufficiently such as dielectric films. As a result, it is necessary to rely on optical reflectance techniques to measure dielectric film thickness.

The optical reflectance of the conducting metal film can vary with surface oxidation and grain size. After a conducting metal film is deposited on a semiconductor wafer, an annealing step is carried out to stabilize the film, to improve the conductivity of the metal film by enhancing the size of the metal grains, and with the proper reduction agent, to clean oxide from the film. This annealing process changes the grain size of the conducting metal film which changes the optical reflectance characteristics and the sheet resistance. The change in film reflectance after annealing can be correlated to both oxide removal and grain size variations.

Moreover, eddy current sensing alone cannot distinguish whether sheet resistance varies because of film thickness or because of grain size change caused by the annealing process. Therefore, both optical reflectance measurements and eddy current sensing measurements are required to adequately determine thickness of a conducting metal film, and it is advantageous to take both measurements during a single inspection. Optical reflectance measurements can compensate for variations in sheet resistance due to grain size variations thereby allowing eddy current sensing measurements to correlate accurately with film thickness.

Both the optical reflectance and the eddy current sensing methods of inspecting conducting film are well known to skilled practitioners of the art. However, each method has been employed separately and apart from the other. In view of the foregoing, it would be desirable to be able to rely on different types of information derived from a combination of both optical reflectance and eddy current sensing measurements.

SUMMARY OF THE INVENTION

One feature of the invention is to provide both optical reflectance and eddy current measurements for determining film thickness. Reflectance measurements are useful to determine grain size, oxidation thickness, and film thickness when the film is transparent or semi-transparent. Both dielectric and conducting films may be inspected using optical reflectance measurements. However, only eddy current sensing techniques are useful in measuring sheet resistance of conducting film which is determinative of film thickness and grain size. Such eddy current measurements are typically made at a distance of a few microns to hundreds of microns from the film and cover an area of 1 to 2 square millimeters.

The inventive design enables both eddy current sensing and optical reflectance measurements to be taken sequentially or simultaneously. When both eddy current and optical reflectance measurements are made by the same sensor, either dielectric or conducting metal films may be inspected without changing the sensor. Thus, manufacturing time is reduced because any time needed to change sensor types to inspect different types of films is eliminated. Further, a film may be inspected while it remains in the process chamber thus eliminating time needed to move a wafer with a deposited film from a process chamber to an inspection chamber. Still further, multiple film layers may be inspected simultaneously provided a transparent dielectric film overlays a conducting metal film.

In accordance with the invention, a two optical fibers (or a bifurcated optic fiber having two channels) and an eddy current inspection coil are provided together. In one embodiment, the fibers may be placed co-axially within the coil. A first optical fiber is connected to either a broadband or a narrowband (laser) light source for illuminating the film. A second optical fiber is connected to a spectrometer or a monochromator which is equipped with a charge coupled device, a photodiode array, or a photodiode with a band pass filter to measure the reflected light intensity returning from the object through the second fiber. Without optical focusing, the area illuminated by the first fiber is about the same area as the area inspected by the eddy current sensor. However, some applications may require a smaller inspection area, and in those cases, a sensor which includes an optical focusing member may be used.

In another embodiment, the first and second optic fibers are mounted external to the eddy current sensor but are focused on the area to be inspected by the eddy current sensor. Connections to the light source and detector remain the same as in the first embodiment.

In still a further embodiment, an array of eddy current—optical reflectance (eddy-optic) sensors may be used to measure the uniformity of a film's properties, or a single such sensor may be used to measure the properties of the film at various locations by effecting relative movement between the sensor and the film, by moving either the sensor, or the film, or both.

BRIEF DESCRIPTION OF THE DRAWINGS

These and other features and benefits of the invention will be readily appreciated in light of the following detailed description of the preferred embodiments thereof, given by way of example only with reference to the accompanying drawings wherein.

DETAILED DESCRIPTION OF THE PREFERRED EMBODIMENTS

Preferred embodiments of the present invention will now be described with reference to the attached drawings, wherein identical elements are designated with like numerals.

Figure 1:
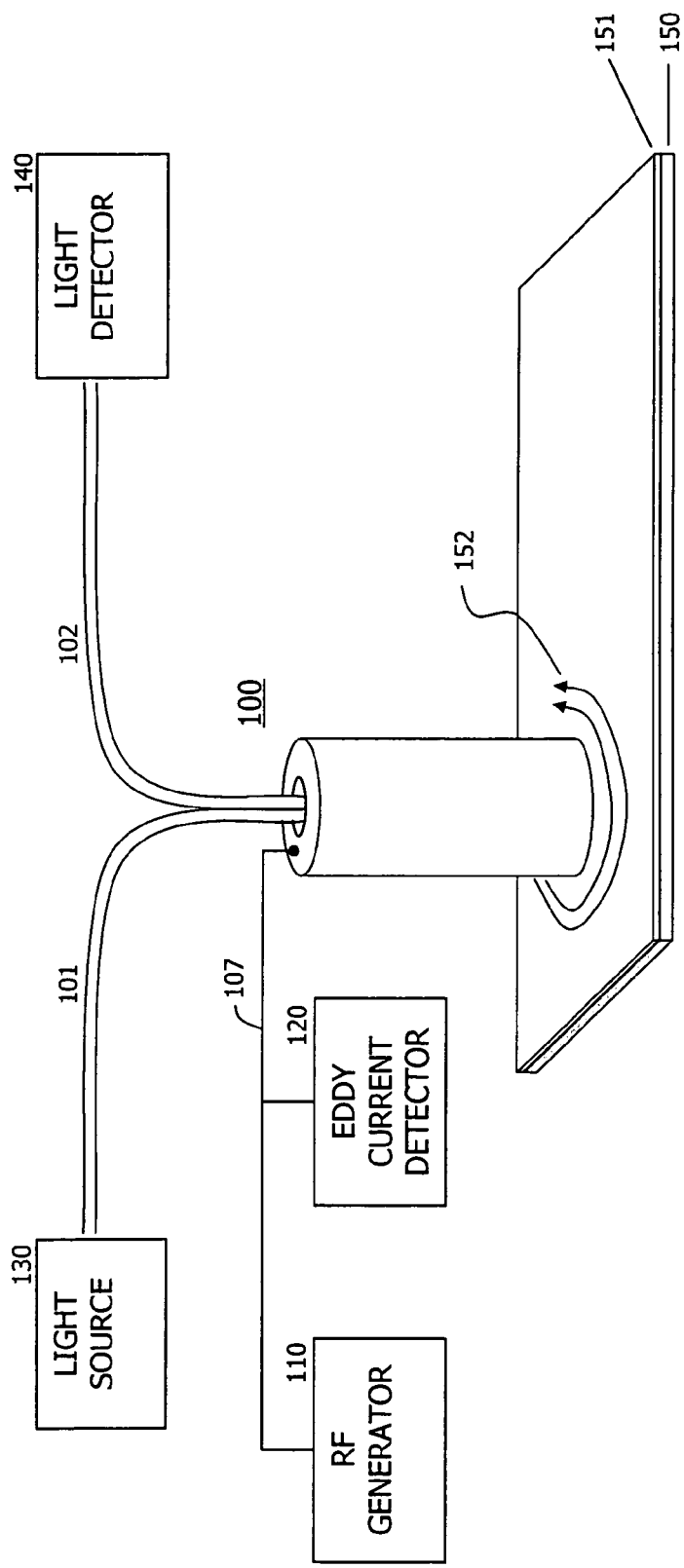
FIG. 1 shows a first embodiment of the inventive sensor.
Figure 2:
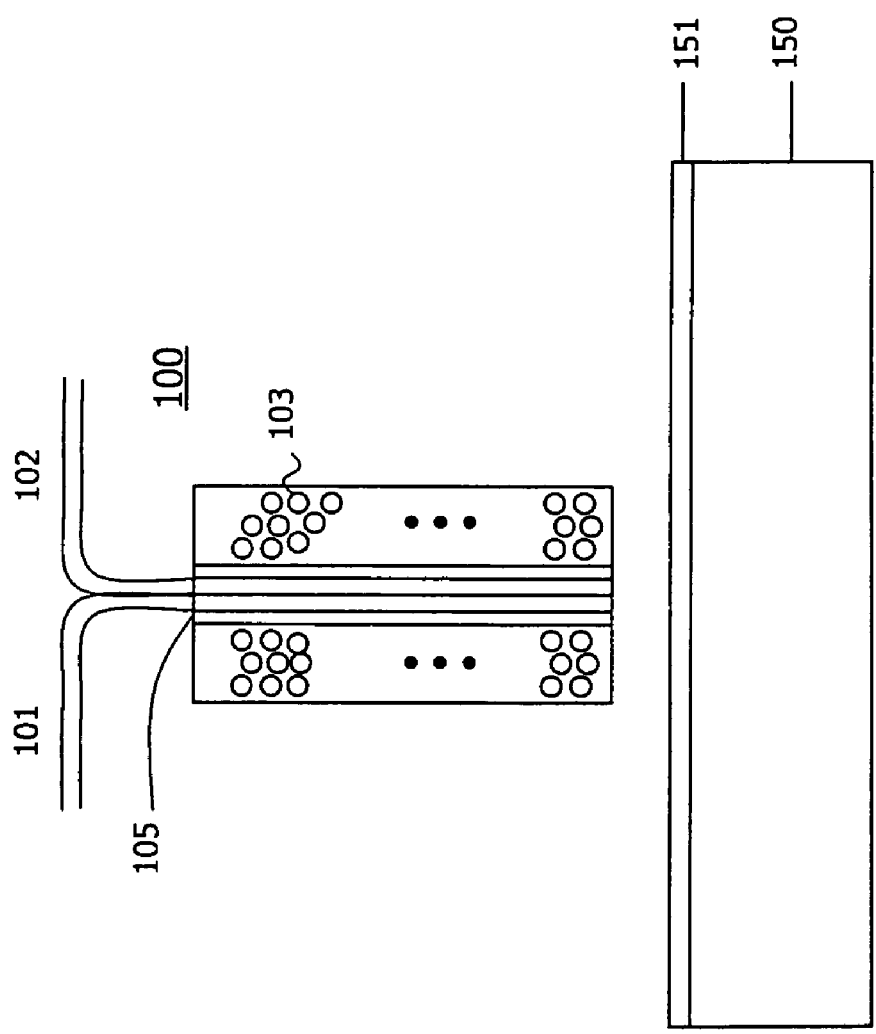
FIG. 2 shows a cross section of the inventive sensor.

The eddy-optic sensor offers clear and distinct advantages over other sensors to measure conducting film thickness. In a typical installation, referring to FIG. 1, a sensor 100 is positioned from a few microns to a few hundreds of microns over an object 150, such as a semiconductor wafer, upon which a conducting film 151 has been deposited. An eddy current inspection coil 103 as shown in FIG. 2 is energized by a radio frequency generator 110 using conductor 107. The eddy current inspection coil 103 induces eddy currents 152 in the conducting film 151 which are then detected by an eddy current detector 120. Measurements taken by the eddy current detector 120 are representative of the resistance of the conducting film 151, and in the case of constant resistance also of the thickness of the film.

The sensor also illuminates the film using a light source 130 which emits light is conducted by a first fiber 101 to a location at which film measurement is to be made. The light source 130 will be either a broadband light source or a laser having a wavelength in the range of 200 to 1100 nanometers (ultraviolet to near infrared). Light reflected by the conducting film 151 then is conducted by a second fiber 102 to a light detector 140. The light detector 140 may be a device such as a charge coupled device or a photodiode array, though any detector suitable for this purpose may be used. Measurements taken by the light detector 140 may be used to determine the thickness, the index of refraction and the index of extinction of transparent or semi-transparent films 151.

Relative distances of the light source 130 and light detector 140 from the film measurement location are not important to the implementation of the invention. Also, while the discussion has been provided in the context of conducting film, the optical reflectance aspect of the invention is also applicable to dielectric films.

As generally illustrated in FIG. 2, a cross sectional view of one construction according to the invention, the first optic fiber 101 and second optic fiber 102 extend into an axial bore 105 of the sensor 100 and is secured therein using an appropriate adhesive. Exemplary dimensions for the sensor 100 shown in FIG. 2 are 10 mm in length and 3 mm in diameter, and having a bore diameter of 0.25 mm, though it is within the contemplation of the invention to vary the dimensions as needed, depending upon the application.

Figure 3:
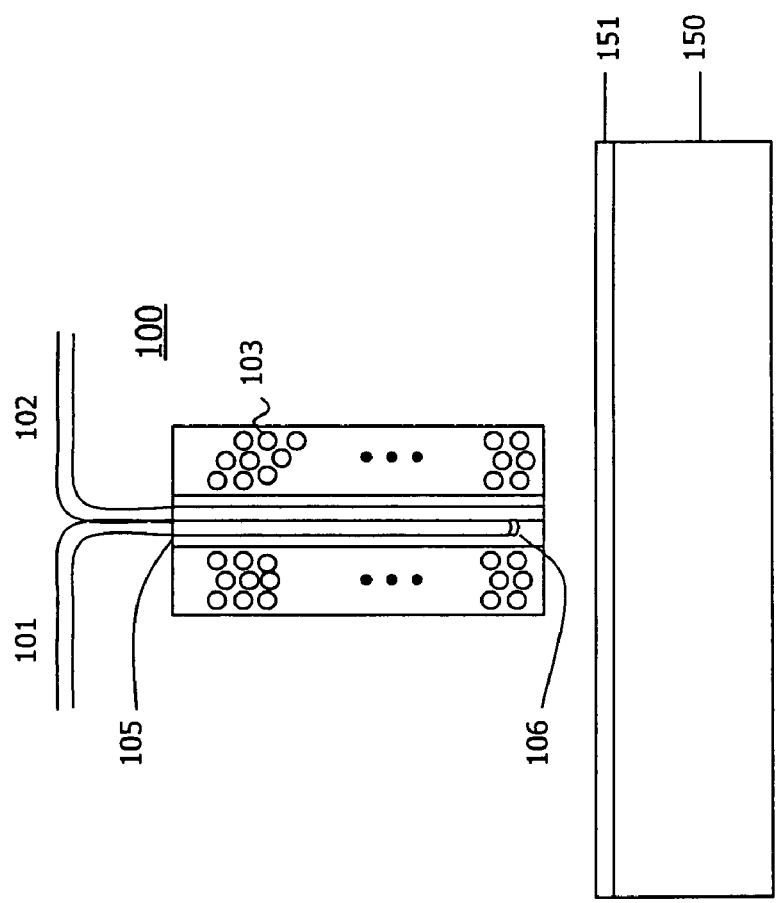
FIG. 3 shows a cross section of the inventive sensor having a focusing member.

In another construction illustrated in FIG. 3, the light conducted by the first fiber 101 is focused by a modifying member 106 and directed to the conducting film 151 under inspection. The modifying member 106 may be attached to the first fiber 101, or to both the first fiber 101 and the second fiber 102.

Figure 4:
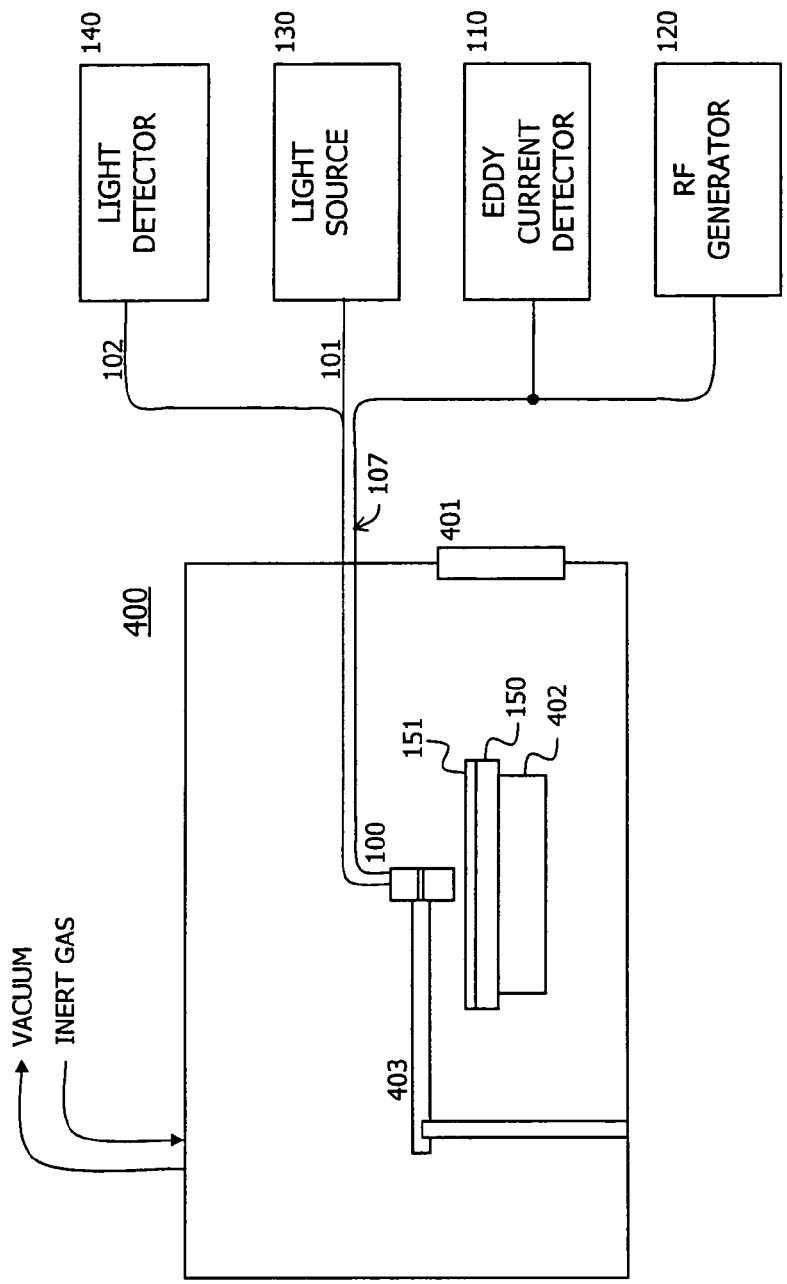
FIG. 4 shows an inspection system using the inventive sensor.

FIG. 4 shows one example of the inventive sensor in the context of a manufacturing process, wherein sensor measurements can be taken in situ, without removing the object from the process. In FIG. 4, an object 150, such as a semiconductor wafer having a conducting film 151 disposed thereon is placed in inspection chamber 400 through an air lock 401. The object 150 is placed on a positioning turntable 402 so that the object 150 may be rotated through 360 degrees if desired. Positioning the object 150 on the positioning turntable 402 may be performed by robotic devices (not shown). The sensor 100 is mounted on a positioning arm 403 that positions the sensor 100 at the correct distance from the object 150 and has the ability to position the sensor 100 over any part of the object 150 and hence over any part of the conducting film 151. Various mechanisms to effect relative movement between the sensor 100 and the object 150 are well known to a skilled artisan. It is envisioned that these mechanisms will adjust the proximity of the sensor 100 to the conducting film 151 and/or adjust the angular or translational position of the positioning arm 403 with respect to the object 150. Any point on the conducting film 151 may be inspected by providing appropriate relative movement between the object 150 and the sensor 100. This relative movement may be effected by moving the object 150 on the turntable 402; moving the sensor 100 on arm 403; or both. Further, the sensor 100 may be tilted relative to the object 150 such that the sensor axis is not perpendicular to the surface of the object 150.

It may be desirable for the inspection chamber 400 to be used for another process of wafer manufacture such as a cool-down, anneal or metal deposition step, wherein eddy-optic inspection may proceed along with the other process, thereby reducing set-up time and increasing overall productivity.

Figure 5:
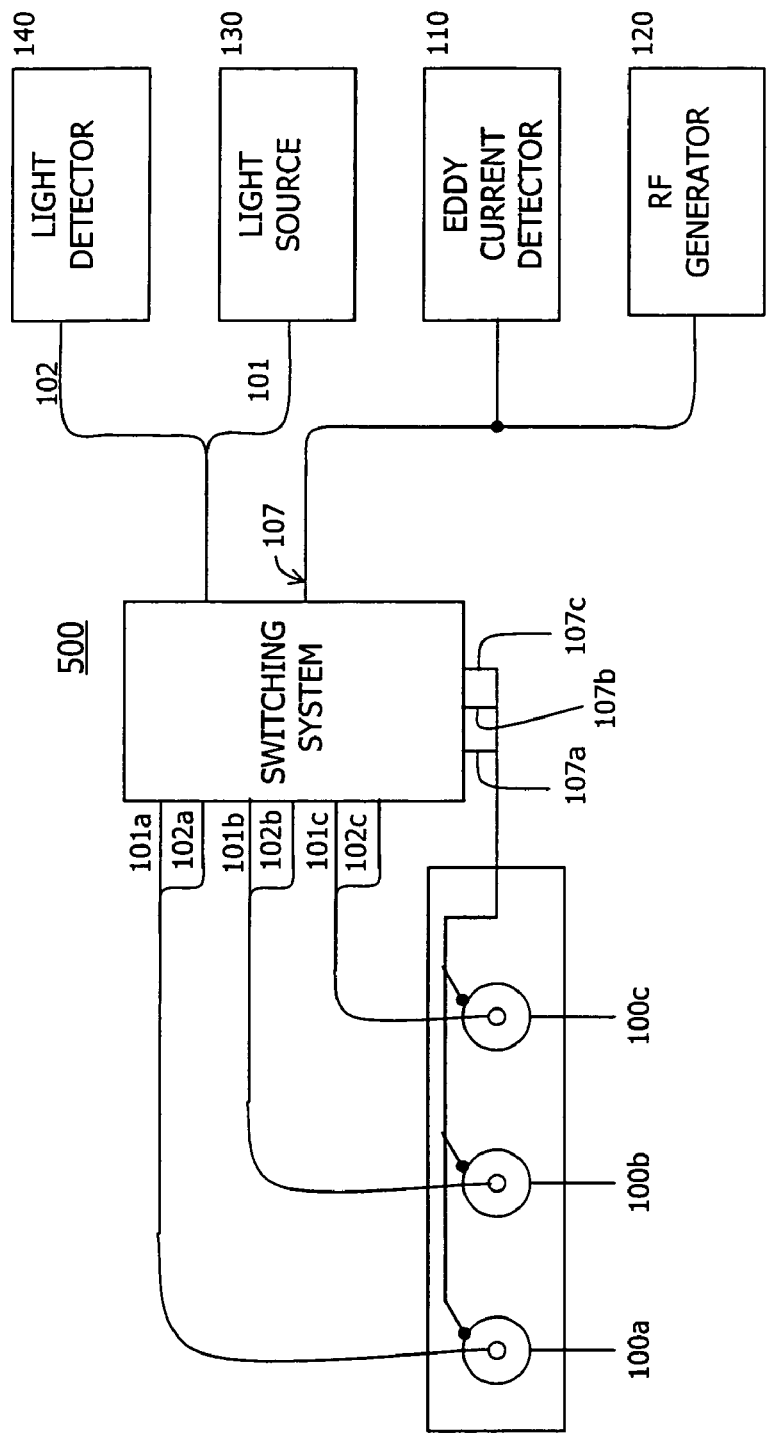
FIG. 5 shows a further embodiment according to the invention.

FIG. 5 shows an array of the inventive sensors which may monitor several locations on a wafer. In FIG. 5, several sensors 100a–100c are mounted on a positioning arm 403. The positioning arm 403 may be any configuration that comports with a desired inspection pattern. Each of the sensors 100a–100c is connected to a switching system 500 using a plurality of first fibers 101a–101c and a plurality of second fibers 102a–102c and conductors 107a–107c such that the switching system 500 may quickly connect an individual sensor to the light detector 140, the light source 130, the eddy current detector 110 and the RF generator 120 either sequentially or in a predetermined sequence. Each of the first optic fibers 101a–10c and the second optic fibers 102a–102c is connected separately to the switching system 500. In such a manner, several locations on the object to be inspected may be quickly and/or selectively examined.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A wafer inspection system comprising:
   a sensor comprising an eddy current inspection coil in communication with a radio frequency generator and an eddy current detector, the sensor further comprising a first optical fiber in communication with a light source to illuminate a wafer to be inspected, the sensor further comprising a second optical fiber in communication with a light detector to detect light reflected from the wafer;
   a chamber configured to house the wafer; and
   a positioner configured to provide relative movement between the sensor and the wafer, the positioner comprising a positioning arm on which the sensor is disposed.

2. An inspection system as claimed in claim 1, wherein the wafer includes a film.

3. An inspection system as claimed in claim 2, wherein said sensor measures a thickness of said film.

4. An inspection system as claimed in claim 3, wherein said film comprises a conducting film.

5. An inspection system as claimed in claim 3, wherein said film comprises a dielectric film.

6. An inspection system as claimed in claim 3, wherein said film comprises a dielectric film and a conducting film.

7. An inspection system as claimed in claim 1, wherein the sensor further comprises a modifying member, in optical communication with said first optical fiber, and configured to focus light from the light source.

8. An inspection system as claimed in claim 1, wherein the sensor further comprises a modifying member, in optical communication with said second optical fiber, and configured to focus light to the light detector.

9. An inspection system as claimed in claim 1, when the first and second optical fibers are disposed parallel to the eddy current inspection coil in said sensor.

10. An inspection system as claimed in claim 1, wherein the first and second optical fibers are disposed co-axially with the eddy current inspection coil.

11. An inspection system as claimed in claim 1, wherein the light source comprises a laser.

12. An inspection system as claimed in claim 11, wherein the light source emits light comprising light having a wavelength in the range from 200 to 1100 nanometers.

13. An inspection system as claimed in claim 1, wherein the light source comprises a broadband light source.

14. An inspection system as claimed in claim 1, wherein the light detector comprises a charge coupled device.

15. An inspection system as claimed in claim 1, wherein the light detector comprises a photodiode array.

16. An inspection system as claimed in claim 1, wherein the positioner further comprises an apparatus for tilting the sensor at an angle with respect to the wafer.

17. An inspection system as claimed in claim 1, wherein the positioner further comprises a positioning turntable on which the wafer is disposed.

18. An inspection system as claimed in claim 1, wherein said system comprises more than one said sensor.

19. A semiconductor processing system comprising:
   a substrate positioner configured to position a semiconductor substrate in the processing system;
   a sensor positioning system configured to position one or more sensors including a first sensor relative to the substrate and to provide relative movement between the one or more sensors and the substrate the sensor positioning system comprising a positioning arm on which the one or more sensors are disposed; and
   wherein the first sensor comprises an eddy current monitoring portion and an optical monitoring portion.

20. The system of claim 19, wherein the positioning arm is configured to position the first sensor at a pre-determined distance from the substrate in the substrate positioner.

21. The system of claim 19, further including an eddy current detection system and a light detection system in communication with at least one of the one or more sensors.

22. The system of claim 19, wherein the one or more sensors further comprises a second sensor, and further including a switching system configured to place the first sensor in communication with the eddy current detection system and the light detection system at a first time, and to place the second sensor in communication with the eddy current detection system and the light detection system at a second different time.

23. The system of claim 19, further including the substrate.

24. The system of claim 1, further including the wafer.

* * * * *